United States Patent [19]

Dotson, Jr.

[11] 4,274,411

[45] Jun. 23, 1981

[54] FLUID OPERATED OPHTHALMIC IRRIGATION AND ASPIRATION DEVICE

[76] Inventor: Robert S. Dotson, Jr., 535 Peabody Sq., Memphis, Tenn. 38104

[21] Appl. No.: 25,537

[22] Filed: Mar. 30, 1979

[51] Int. Cl.$^3$ ............................................. A61M 1/00
[52] U.S. Cl. .................................. 128/276; 128/910; 433/95
[58] Field of Search ............... 128/276, 277, 278, 910; 137/205; 251/5; 32/33

[56] References Cited

U.S. PATENT DOCUMENTS

| | | | |
|---|---|---|---|
| 3,589,363 | 6/1971 | Banko et al. | 128/276 |
| 3,682,166 | 8/1972 | Jawbs | 128/276 |
| 3,730,180 | 5/1973 | Davison | 128/204.24 |
| 3,885,567 | 5/1975 | Ross | 128/278 |
| 3,932,065 | 1/1976 | Ginsberg et al. | 251/5 |
| 4,041,947 | 8/1977 | Weiss et al. | 128/276 |
| 4,052,987 | 10/1977 | Wochinich et al. | 128/276 |
| 4,136,700 | 1/1979 | Broadwin et al. | 128/276 |

FOREIGN PATENT DOCUMENTS 254223 12/1923 Fed. Rep. of Germany ........... 128/910

Primary Examiner—Robert W. Michell
Assistant Examiner—J. L. Kruter
Attorney, Agent, or Firm—Ernest B. Lipscomb, III

[57] ABSTRACT

A fluid operated and controlled irrigation and aspiration device for ophthalmic use. A source of fluid under pressure is connected through foot pedal operated valves to clamps for controlling irrigation through a conventional handpiece, and to a vacuum generating device. Selecting valves are provided for isolating the vacuum generating means, and for directing pressure to a pulsing circuit. The pulsing circuit can be used to control the vacuum to yield a pulsing aspiration; and, in a modification of the device, the pulsing circuit can be used to control a pressure circuit to operate a cutting device.

5 Claims, 3 Drawing Figures

FLUID OPERATED OPHTHALMIC IRRIGATION AND ASPIRATION DEVICE

This invention relates generally to ophthalmic equipment, and is more particularly concerned with fluid operated control means for an irrigation and aspiration device for intraocular use.

When a surgeon is to cut into the eyeball of a patient, he must have constant irrigation, or flow of liquid into the eye. This is necessary, and very critical, because it is important to maintain the proper pressure within the eyeball since a lowering of pressure can cause numerous problems. Furthermore, in an operation such as a cataract removal, there is a certain amount of material to be removed from the eye, and this material can frequently be removed by aspiration equipment, or simply applying a vacuum through a needle or other appropriate implement to remove the unwanted material.

The removal of the cataract is actually the removal of at least part of the lens from the eye, and there are several means by which the removal can be accomplished. Perhaps the most common technique for removal of the lens is to prolapse the solid components of the lens, which is the physical removal of the material through an appropriate surgical opening. Recently, there have been devices to break up the lens using ultrasonic energy. In this technique, the lens is completely fragmented using high frequency sound waves, then the debris is aspirated. While this technique is thorough, and requires relatively little effort on the part of the surgeon, there is some hazard in that high energy waves are propagated into the eye where a small error could cause irreparable harm.

In numerous pieces of ophthalmic equipment, the equipment has been electrically operated. The usual apparatus includes electrical controls for the supply of irrigating fluid, an electric pump to create a vacuum, and electrical controls for variation and application of the vacuum. While this prior art equipment works satisfactorily, it will be understood that the equipment is subject to the electrical power available. Thus, exceptionally low voltages may cause poor operation of the equipment, and exceptionally high voltages may damage the equipment and/or cause improper operation. Furthermore, there are instances when electric power is simply not available, which would mean that the prior art equipment simply cannot be used. Additionally, the prior art equipment has been extremely expensive, and there is of course the inherent hazard of sparks so that the prior art electrical equipment could not reasonably be used in an explosive atmosphere.

The present invention overcomes the abovementioned and other difficulties with the prior art irrigation and aspiration apparatus by providing a completely fluid operated control unit that will provide irrigation and aspiration for intraocular work. The apparatus of the present invention includes selective control means to provide irrigation alone, or irrigation and aspiration, the control means being conveniently located for operation by the surgeon. The amount of vacuum can be pre-set so that any time aspiration is required, the same pressure will be achieved. The aspiration circuit is further provided with a pulsing system wherein the vacuum will cycle between the maximum vaccum selected and the minimum vacuum. This vaccum pulsing circuit can be used to assist in aspirating difficult material; and, the pulsing circuit can be used to operate a conventional intraocular cutting device.

These and other features and advantages of the present invention will become apparent from consideration of the following specification when taken in conjunction with the accompanying drawing in which.

Figure 1:
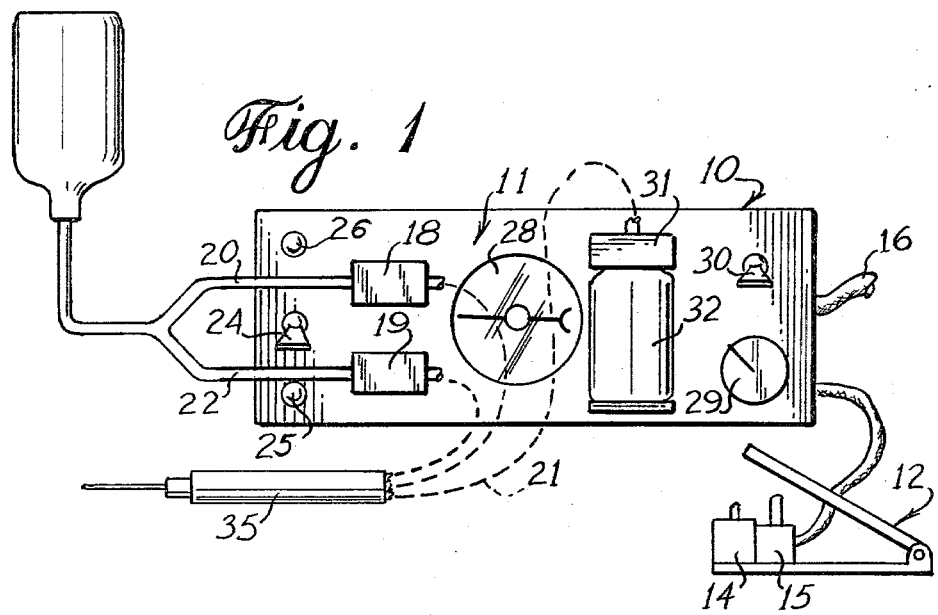
FIG. 1 is a perspective view showing an irrigation and aspiration device made in accordance with the present invention.

Referring now more particularly to the drawing, and to those embodiments of the invention here chosen by way of illustration, it will be seen that the device includes a cabinet 10 having a front panel 11 which carries the various controls to be manipulated by the surgeon, and which will be discussed in more detail hereinafter. The device also includes a foot pedal generally designated at 12 and including a pair of valves 14 and 15 connected to the cabinet 10 by appropriate tubing. A supply tubing 16 is provided for connection to a source of fluid under pressure.

Though the specific design of the apparatus is subject to some engineering changes, it should be generally understood that the source of fluid under pressure can be almost any usual source. When working in a large, well-equipped hospital, the appropriate pressure will probably be available in a conventional wall connection; however, a cylinder of gas will also operate the device of the present invention.

In one successful model of the present invention, the apparatus will operate on a pressure as low as 25 psi, and this pressure can be supplied by almost any bottle, cannister or the like. As a result, the apparatus of the present invention is very portable, and can be used in any country without adaptation to local power, and can be used in remote rural areas where no electric power is available.

The front panel 11 of the housing 10 includes a pair of tubing clamps 18 and 19. As will be discussed more fully hereafter, the clamp 18 is used to control irrigation fluid when the device is utilized to provide both irrigation through a tubing 20 and aspiration through a tubing 21. The tubing clamp 19 is used to control irrigation when only irrigation is to be used through the tubing 22. A control lever 24 extending from the front panel 11 allows the surgeon to select between the two modes of operation, and there are two indicators 25 and 26 to provide a visual indication of the mode that has been selected.

Generally centrally of the front panel 11, there is a vacuum gauge 28 which will indicate the amount of vacuum being used during the procedure. The amount of vacuum is controlled by a control knob 29; and, above the knob 29 there is a selector 30 which allows the surgeon to select between a continuous vacuum and a pulsing vacuum.

The aspiration line 21 is connected to the specimen bottle holder 31. It will be understood that the arrangement is such that the specimen bottle 32 will be evacuated, and material will flow through the line 21 and into the specimen bottle 32 so that liquid and solids will remain in the specimen bottle 32 while air will pass into the vacuum system.

A handpiece 35 is here illustrated; however, it should be understood that the particular handpiece 35 forms no part of the present invention, but the apparatus of the present invention may be used with numerous conventional handpieces such as the handpiece 35.

Figure 2:
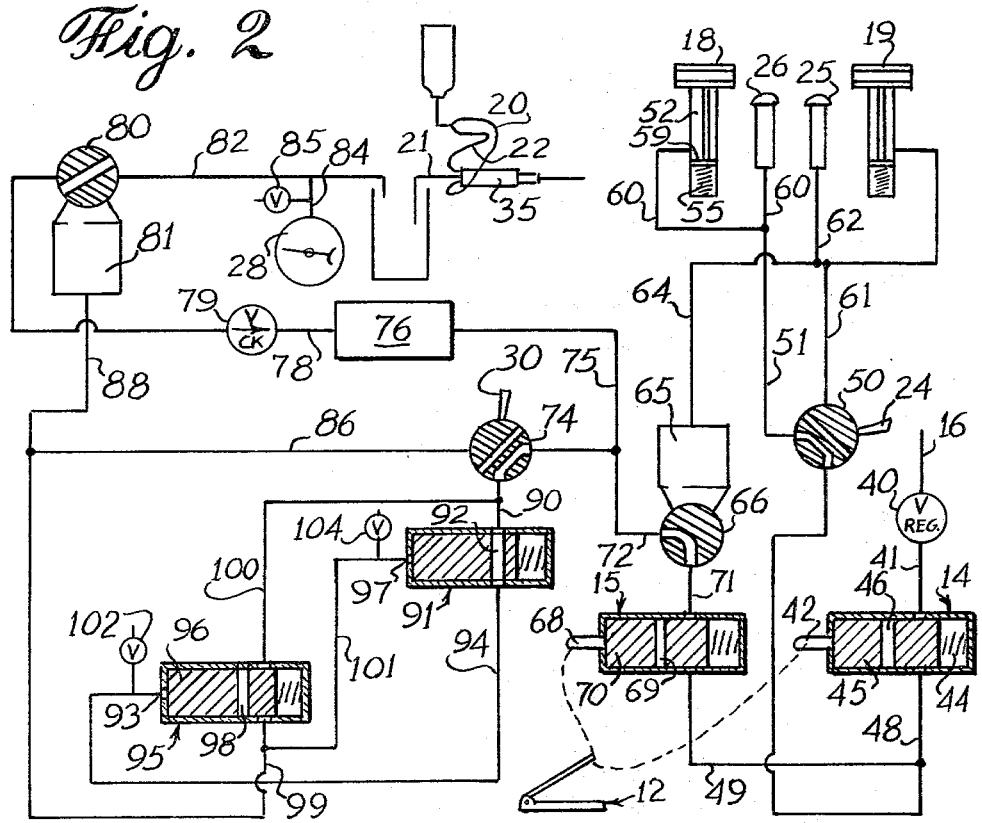
FIG. 2 is a schematic diagram showing the irrigation and aspiration fluid circuits and the control circuits for use in the device shown in FIG. 1; and, FIG. 3 is a view similar to FIG. 2 showing a modified form of circuit designed to operate an intraocular cutting device.

Attention is now directed to FIG. 2 of the drawing for an understanding of the internal construction and operation of the apparatus shown in FIG. 1.

In FIG. 2 it will be seen that a source of fluid under pressure is connected to the line 16. The fluid passes through a valve 40 which is adapted to regulate the incoming pressure. From the valve 40, a line 41 is connected to the valve 14 in the foot pedal 12. The valve 14 includes a plunger 42 for actuating the valve, and the spring 44 causes the valve to return to its normal position. As is shown schematically, when the valve 14 is in its normal position, fluid flow is blocked so that there is no flow from the tube 41 to the valve 14; however, when the plunger 42 is depressed the valve body 45 is shifted so that the opening 46 is aligned with the tube 41 and fluid can flow from the tube 41, through the opening 46 of the valve body 45, and to the connecting tubing 48.

The foot pedal 12 has three positions. When the foot pedal 12 is in its uppermost position, the apparatus is off; when the foot pedal is in its second position, the apparatus is arranged for irrigation only; and this second position causes the depression of the plunger 42 to actuate the valve 14.

It will be seen that the tubing 48 has a branch 49 which leads to the valve 15; however, the valve 15, in its normal position, does not allow fluid to flow therethrough. The tubing 48 connects to a toggle valve 50 which is controlled by the selector 24. It will be remembered that the selector 24 allows the surgeon to select between irrigation and aspiration, or irrigation only. Thus, the valve 50 has two positions, and the valve 50 is shown in the position that would allow both irrigation and aspiration. For this function, the tubing 48 will be connected through the valve 50 to the tubing 51. When fluid under pressure is admitted into the cylinder 52 it will be understood that a piston 59 will be moved against the tension of the spring 55 and release the clamping pressure of the tubing clamp 18. Simultaneously, pressure would extend through the tubing 60 and to the indicator 26 to indicate which tubing clamp is actuated.

If the valve 50 is in its opposite position, the tubing 48 will be connected to a tubing 61 which leads to the tubing clamp 19, a branch 62 leading to the indicator 25. The important functional difference is achieved by a branch line 64 which is connected to a fluid control means 65 for a valve 66. This will be discussed in more detail below.

Returning now to the valve 15, it will be understood that, when the foot pedal 12 is further depressed to its third position, both the plunger 42 on the valve 14 and the plunger 68 on the valve 15 will be depressed. The valve 14 will allow fluid to flow therethrough as has been previously discussed; and, similarly, the valve 15 will be shifted so that the passageway 69 in the valve body 70 is aligned with the tubing 49 so that the tubing 49 is connected, through the passageway 69, to the tubing 71, thence to the valve 66.

The valve 66 is a normally-open valve so that, once the valve 15 is shifted to allow fluid to flow therethrough, fluid will also flow through the valve 66 and to the tubing 72. If the valve 50 is in its shifted position so that irrigate-only has been selected, pressure from the line 64 will operate the control device 65 to shift the valve 66 and prevent the flow of fluid through the valve 66. Since the tubing 72 leads to the aspiration actuating apparatus, closing of the valve 66 will prevent any aspiration.

It will therefore be seen from the foregoing that, with an appropriate source of fluid under pressure connected to the tubing 16, and the valve 40 adjusted to regulate the pressure, the valve 50 can be manipulated to allow the surgeon to select one position in which both irrigation and aspiration will be available on the handpiece 35, and another position in which irrigate-only will be available. Furthermore, even though the valve 50 is in a position for both irrigation and aspiration, the foot pedal 12 can be depressed to its second position to open the valve 14 while leaving the valve 15 closed, and there will be only irrigation; however, the foot pedal 12 can be further depressed to its third position thereby opening valves 14 and 15, and both irrigation and aspiration will be available at the handpiece 35, the aspiration being provided by the remainder of the apparatus to be discussed in conjunction with FIG. 2 of the drawing.

The line 72 is connected to a toggle valve 74 which can be operated by the control 30. It will be remembered that the control 30 allows the surgeon to select between a constant vacuum and a pulsing vacuum. As the valve 74 is shown in the drawing, the device would produce the pulsing vacuum, but the valve can be shifted to provide a constant vacuum, and the constant vacuum circuit will be discussed first.

From the line 72, there is a branch 75 which leads to a vacuum generator 76. It will be understood that there are numerous forms of apparatus that can create a vacuum through the use of fluid under pressure. Obvious means are conventional vacuum pumps operated by fluid driven motors, or the use of a conventional aspirator utilizing the venturi effect. Other means will suggest themselves to those skilled in the art. The only important thing with respect to the present invention, however, is that a device 76 receives fluid under pressure from the line 75 and creates a vacuum on the connecting line 78.

The line 78 is provided with a check valve 79 which is important in the present device simply as a safety feature. It will be realized that a reverse flow through the vacuum line 78 could cause excessive pressure through the handpiece 35 so the check valve 79 is provided to assure that there will be no reverse flow through the vacuum line 78.

The line 78 also contains a normally closed valve 80 which can be opened using the fluid operated means 81. The valve 80 is connected to a line 82 which has a branch 84 leading to the vacuum gauge 28; and, it will be seen that the branch 84 contains a needle valve 85 open to the atmosphere. The needle valve 85 is manipulated by means of the knob 29 on the face of the panel. It will therefore be seen that, by manipulating the knob 25 to vary the needle valve 85, the level of vacuum in the tube 82 will be varied, and the amount of vacuum will be readable on the vacuum gauge 28. This vacuum is also connected to the specimen bottle 32 whereby the vacuum is applied to the line 21 which is connected to the handpiece 35 as previously discussed.

In order to open the valve 80 and allow the vacuum from the line 78 to be connected to the line 82, it will be seen that the valve 74 can be shifted to its alternate position so that the line 72 is connected to the line 86. The line 86 is connected to the line 88 which leads directly to the device 81 for manipulation of valve 80.

It will now be seen that, when the foot pedal 12 is depressed to its third position, the plunger 68 will be moved to align the passageway 69 with the tubing 49 and allow fluid to flow from the tubing 49, through the passageway 69 and through the tubing 71 to the valve 66. If the valve 66 is open as is shown in the drawing, fluid will pass through the valve 66 and into the line 72, thence through valve 74 and through the lines 86 and 88 to operate the device 81 and open the valve 80. When the foot pedal 12 is released to allow the valve 15 to close, the pressure through the lines will be released and the valve 80 will be automatically returned to its normally closed position.

The pulsing circuit is made up of a pair of cooperating valves which are arranged to operate each other. It will be seen that, from the valve 74, there is a line 90 which leads to a valve 91. In its normal position, the valve 91 has a passageway 92 in alignment with the input line 90 so that fluid can flow from line 90, through the passageway 92 and into the output tubing 94. The tubing 94 is connected to the operating port 93 of the valve 95; and, when pressure is admitted from the tubing 94 into the valve 95, the valve body 96 will be shifted to the right from the position shown in the drawing, so that the passageway 98 will be aligned with the output and input tubings 99 and 100.

It should first be understood that initial fluid flow into the line 90 will flow through the valve 91 and into the tubing 94 to operate the valve 95, but the valve 95 is closed so that no fluid can flow from the line 90, through the input line 100 and through the valve 95.

Returning now to the operation of valve 95 it will be understood that the operation of valve 95 will allow fluid to flow from the line 90, through the input tubing 100, through passageway 98 of the valve 95, then to output tubing 99 and through the branch 101 and to the operating port 97 of the valve 91. The admission of fluid under pressure to the valve 91 will cause the valve body of the valve 91 to shift to the right so that the passageway 92 will no longer be aligned with the tubing 90, and fluid under pressure will no longer be admitted to the operating port 93 of valve 95. It will be realized that fluid under pressure is at this point admitted from the line 90, through the line 100 and through the passageway 90 of the valve 95, then to the tubing 99 which is connected to the line 88. As a result, when the valve 95 is shifted to allow fluid pressure on the line 99, the valve 80 will be opened to place a vacuum on the line 82.

Returning to the valve 91, it will be understood that, since the valve 91 has been shifted to remove pressure from the tubing 94, there is no longer a pressure to hold the valve 95 in its open position so the spring will return the valve 95 to the position shown in the drawing. The speed with which the valve body 96 in the valve 95 returns is variable by manipulating the needle valve 102. Since the fluid must exit from the valve 95 through the valve 102, adjustment of the valve 102 will vary the speed with which the fluid can be dissipated. Once the valve body 96 in the valve 95 returns to its position as shown in the drawing, the fluid pressure in the line 88 will be removed so that the valve 80 will be returned to its "off" position and vacuum on the line 82 will be terminated. The return of the valve 95 to its normal position will also remove pressure from the operating port 97 so that the valve 91 also returns to its normal position under the influence of its spring, and as controlled by a needle valve 104. Once the valve 91 has fully returned to its position as shown in the drawing, the entire process will be repeated. It will therefore be seen that when the valve 74 is in the position as shown in the drawing, the pressure in the line 88 will be cyclical as the valves 91 and 95 shift back and forth as described. The cyclical pressure on the line 88 will cause opening and closing of the valve 80, hence cyclical vacuum on the line 82.

Figure 3:
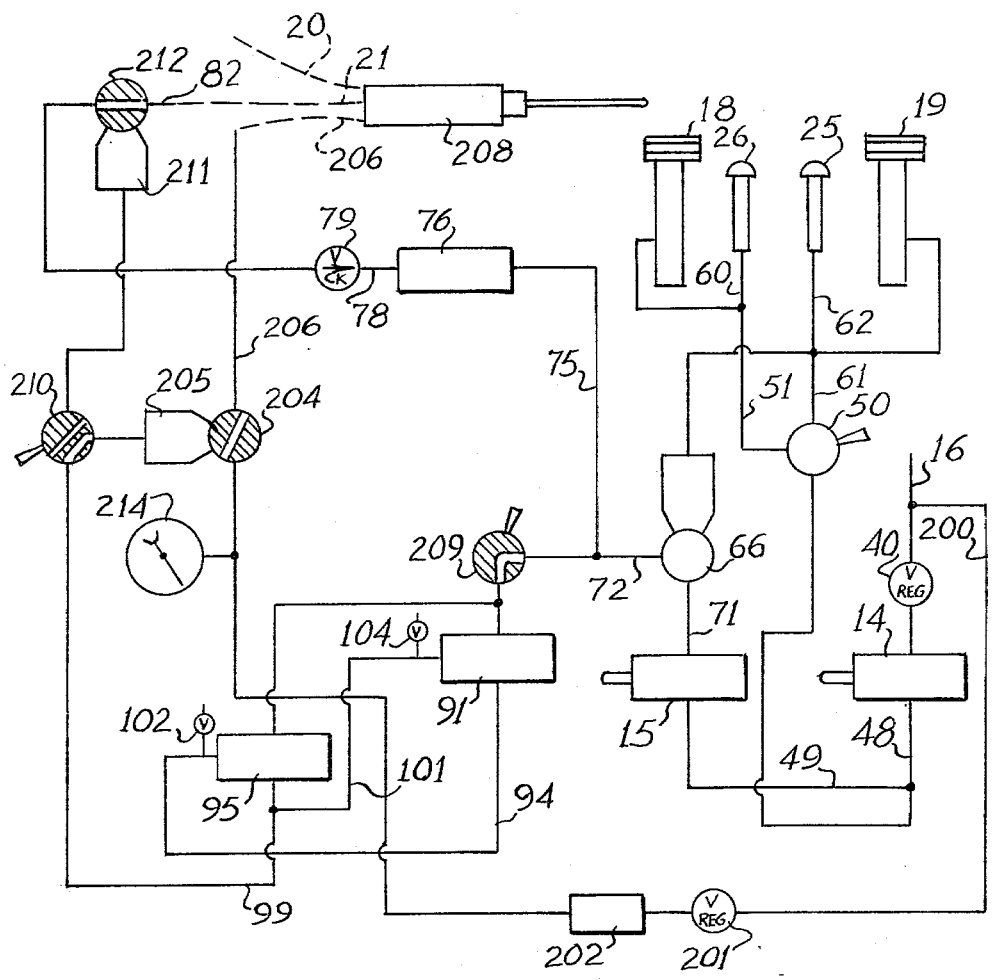

Attention is next directed to FIG. 3 of the drawing which shows a modification of the control circuit shown in FIG. 2, the circuit of FIG. 3 being arranged to operate an intraocular cutting device. Since much of the circuit of FIG. 3 is like the circuit of FIG. 2, the same reference numerals have been used for the same parts, and the description will not be repeated for the common parts of the circuit.

It will be understood by those skilled in the art that cutting devices are available for intraocular use, and these cutting devices are frequently built into a handpiece similar to the handpiece 35. A needle is provided for insertion into the eye through an appropriate surgical opening; and, the needle has an opening to receive a piece of tissue, and a relatively moveable cutting means to sever the tissue. The moveable cutting means is operated by fluid pressure, and a vacuum is frequently provided so that pieces of tissue can be aspirated as they are severed. These conditions render the control means of the present invention admirably suited to control of such an intraocular cutting device.

Looking now particularly at the control means shown in FIG. 3, it will be seen that the supply tubing 16 is provided with a branch tube 200 connected before the valve 40. The tube 200 then has its own regulator valve 201 so that a different pressure can be set for the valve 14 and for the cutter control.

The source of fluid under pressure may be generally from about 25 psi to about 150 psi, so there is available a range to operate most any device to be used in conjunction with the present apparatus. The apparatus previously described may operate on about 25 psi, and a cutter for operation by the cutter circuit may operate on about 15 psi. Other apparatus may require different pressures, and the control circuit of the present invention can provide virtually any pressure required as long as the source has at least the required pressure.

Following the regulator valve 201, there is a filter 202 in the line 200 to assure that no foreign material passes through the line 200 and into the cutting device. For greatest convenience, it is desirable that the filter 202 have an expendable cartridge, though of course numerous forms of filter may be used.

From the filter 202, the tube 200 is connected to a valve 204 which is operable by a fluid operating device 205. As is shown schematically, the valve 204 is normally closed, and actuation of the operating device 205 will open the valve. Cessation of fluid pressure to the operating device 205 will allow the valve 204 to close under the influence of its own operating mechanism.

From the valve 204, a line 206 is connected to the handpiece 208. As previously discussed, it will be understood that the handpiece 208 is a conventional device having a cutting means to be operated by fluid pressure, aspiration means operated by a vacuum line, and irrigation means for delivering irrigation fluid therethrough. It will therefore be understood that the vacuum line 82 will provide the needed aspiration, and the irrigation lines 20 and/or 22 will provide the irrigation. When the operating device 205 is actuated by fluid pressure, the pressure through the line 200 will be connected to the line 206 so cutter operating pressure will be applied to the handpiece 208.

Looking next at the pulsing circuit, it will be seen that the foot pedal controlled valves 14 and 15 are arranged as previously described so that the valve 14 can be opened to provide irrigation only, or the valves 14 and 15 can be opened to provide both irrigation and aspiration. In the present modification, however, the line from the valve 66 is connected to a valve 209 which will either isolate the pulsing circuit or will connect the pulsing circuit. It should be noticed that the line 75 is arranged as before so that a vacuum is created on the line 78.

The pulsing circuit is as previously discussed, including the valves 91 and 95 which control each other for shifting back and forth to cause a pulsing, or cyclical, pressure on the line 99. It will be seen that the line 99 is connected to a valve 210 which has one position (as illustrated) wherein the pulsing pressure is connected to the operating device 205 for the valve 204, and another position wherein the pulsing pressure is connected to the operating device 211 for the valve 212.

Whereas, in the circuit shown in FIG. 2 the control valve for the vacuum line 82 was a normally closed valve, the valve 212 is a normally open valve. When pressure actuates the operating device 211, the valve 212 will be closed. The reason for this arrangement will appear shortly.

It will now be understood that, when a handpiece 208 having a cutting device is to be used, the handpiece 208 would be appropriately connected, and the valve 201 would be adjusted until the pressure gauge 214 indicates the desired pressure.

When a constant vacuum is desired, the valve 209 would be placed in its "off" position to isolate the pulsing circuit, and a steady vacuum will be provided through the line 82 and the normally open valve 212.

If a pulsing vacuum is desired, the valve 209 would be placed in the position shown in the drawing so fluid pressure is allowed to operate the pulsing circuit as described above. The result will be a pulsing pressure on the line 99. Thus, if the valve 210 is positioned to direct the pulsing pressure to the operating device 211, the valve 212 will be closed cyclically to yield a pulsing vacuum on the line 82.

When a pulsing pressure is to be used to operate a cutter, the usual procedure is to provide a constant vacuum to aspirate the tissue cut off. Thus, the valve 209 would be in the position shown in the drawing so the pulsing circuit will be operated, providing a pulsing pressure on the line 99 at the valve 210. The valve 210 would then be set so the pulsing pressure is directed to the operating device 205 for the valve 204 and away from the operating device 211 for the valve 212. The result is that the valve 204 is cyclically opened to provide a pulsing pressure on the line 206, and the valve 212 remains open to allow a constant vacuum on the line 82.

From the foregoing description, it should be understood that the apparatus of the present invention provides a very simple device that is entirely fluid operated, yet the device provides great versatility in that the surgeon can select a handpiece 35 that is for irrigation only, and the valve 50 can be placed in the position such that the aspiration circuitry is isolated. In this condition, regardless of the depression of the foot pedal 12, and the consequent position of the valves 14 and 15, there can be no aspiration. On the other hand, the surgeon can select a handpiece 35 that is adapted for both aspiration and irrigation, and the surgeon can select, by depression of the foot pedal 12, whether he would like to have irrigation alone, or irrigation and aspiration. When the apparatus is in condition for aspiration, at any time during the procedure, the surgeon can manipulate the device 30 to operate the valve 74 and place the device in condition for a constant aspiration, or in condition for a pulsing aspiration. If the modification shown in FIG. 3 is used, the surgeon may select a handpiece with irrigation and aspiration in addition to a cutting device. Selection by means of the valve 210 allows use of the cutter, or use of the irrigation alone or with aspiration.

The apparatus of the present invention is therefore admirably suited to a variety of ophthalmic techniques and procedures. It will be understood that the present apparatus is admirably adapted to intraocular procedures on pets or other animals as well as humans. When performing operations to remove cataracts from animals, an extracapsular technique is generally used; that is, the nucleus of the lens is removed, the cortical material is removed, and the anterior segment of the capsule is removed, but the posterior segment is left in place. If the posterior segment is removed, there is a great danger of losing some of the vitreous humor, which is frequently fatal to eyesight. The apparatus of the present invention allows the cortical material to be aspirated, and the anterior segment of the lens will frequently fragment so that it too can be aspirated. In the event there is some tissue that is difficult to aspirate, the pulsing circuit can be used to jog the tissue through the needle.

It will of course be understood by those skilled in the art that the apparatus here disclosed is by way of illustration only, and is meant to be in no way restrictive; therefore, numerous changes and modifications may be made, and the full use of equivalents resorted to, without departing from the spirit or scope of the invention as defined in the appended claims.

I claim:
1. An ophthalmic irrigation and aspiration device comprising;
    (a) a source of irrigation liquid,
    (b) a vacuum source,
    (c) a handpiece, including a needle for insertion into the site of use, said handpiece being adapted to carry outlets for the irrigation liquid and the vacuum from the respective sources thereof,
    (d) a vacuum control valve for selectively connecting said vacuum outlet in the handpiece to said vacuum source,
    (e) pulsing means for cyclically operating said vacuum control valve,
    (f) irrigation control means for controlling the flow of said irrigation liquid through the outlet for irrigation liquid in said handpiece, characterized in that said irrigation control means includes first clamping means for stopping the flow of said irrigation liquid through said handpiece,
    (g) aspiration control means for controlling the application of said vacuum source through said handpiece,
    (h) fluid operated means for releasing said first clamping means,
    (i) a source of fluid under pressure,

(j) first valve means for selectively connecting said source of fluid under pressure to said fluid operated means for releasing said first clamping means,
(k) a fluid operated vacuum generating device,
(l) a second valve for selectively directing fluid under pressure from said first valve to said vacuum generating device,
(m) a first toggle valve for selectively connecting said fluid under pressure to said pulsing means and to said vacuum control valve,
(n) said pulsing means including a first fluid operated valve having an input, an output, and a valve operating port, a second fluid operated valve having an input, an output, and a valve operating port,
(o) said output of said first fluid operated valve being in communication with said valve operating port of said second fluid operated valve, and
(p) said output of said second fluid operated valve being in communication with said valve operating port of said first fluid operated valve, said output of said second fluid operated valve being connected to said vacuum control valve.

2. An ophthalmic irrigation and aspiration device as claimed in claim 1, characterized in that said pulsing means includes a first fluid operated valve communicating with said fluid under pressure, a second fluid operated valve for directing said fluid under pressure to said vacuum control valve, said first fluid operated valve comprising means for opening said second fluid operated valve, said second fluid operated valve comprising means for closing said first fluid operated valve.

3. An ophthalmic irrigation and aspiration device as claimed in claim 2 wherein said handpiece includes a cutter, and characterized by pulsing pressure emitted by said pulsing means, a toggle valve for selectively connecting said pulsing pressure to said vacuum control valve and to a cutter tubing valve for cyclically operating said cutter tubing valve.

4. An ophthalmic irrigation annd aspiration device as claimed in claim 1, and further characterized by first variable valve means for allowing dissipation of fluid through said valve operating port of said first fluid operated valve, and second variable valve means for allowing dissipation of fluid through said valve operating port of said second fluid operated valve.

5. An ophthalmic irrigation and aspiration device comprising:
(a) a source of irrigation liquid,
(b) a vacuum source,
(c) a handpiece, including a needle for insertion into the site of use, said handpiece being adapted to carry outlets for the irrigation liquid and the vacuum from the respective sources thereof,
(d) a vacuum control valve for selectively connecting said vacuum outlet in the handpiece to said vacuum source,
(e) pulsing means for cyclically operating said vacuum control valve,
(f) irrigation control means for controlling the flow of said irrigation liquid through the outlet for irrigation liquid in said handpiece, characterized in that said irrigation control means includes first clamping means for stopping the flow of said irrigation liquid through said handpiece,
(g) aspiration control means for controlling the application of said vacuum source through said handpiece,
(h) fluid operated means for releasing said first clamping means,
(i) a source of fluid under pressure,
(j) first valve means for selectively connecting said source of fluid under pressure to said fluid operated means for releasing said first clamping means,
(k) a second clamping means for stopping the flow of said irrigation fluid to said handpiece,
(l) second fluid operated means for releasing said second clamping means,
(m) a toggle valve means for selectively connecting said first clamping means and said second clampng means to said fluid under pressure,
(n) a second fluid controlled valve,
(o) tubing means connection said second fluid controlled valve to fluid under pressure in said second fluid operated means for closing said second fluid controlled valve, and
(p) said second fluid controlled valve being interposed between said second valve and said vacuum generating device.

* * * * *